US008541005B2

(12) United States Patent
Chung et al.

(10) Patent No.: US 8,541,005 B2
(45) Date of Patent: Sep. 24, 2013

(54) CYSTEINE-TAGGED STREPTOCOCCAL PROTEIN G VARIANT

(75) Inventors: Bong Hyun Chung, Daejeon (KR); Jeong Min Lee, Daejeon (KR); Sun-Ok Jung, Gwangju (KR); Yongwon Jung, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 774 days.

(21) Appl. No.: 12/306,903

(22) PCT Filed: Jun. 20, 2007

(86) PCT No.: PCT/KR2007/002996
§ 371 (c)(1),
(2), (4) Date: Mar. 10, 2009

(87) PCT Pub. No.: WO2008/016221
PCT Pub. Date: Feb. 7, 2008

(65) Prior Publication Data
US 2010/0173430 A1 Jul. 8, 2010

(30) Foreign Application Priority Data

Jun. 27, 2006 (KR) .................. 10-2006-0058123
May 30, 2007 (KR) .................. 10-2007-0052560

(51) Int. Cl.
*A61K 39/09* (2006.01)
*A61K 39/085* (2006.01)
*C12Q 1/00* (2006.01)

(52) U.S. Cl.
USPC .............. 424/237.1; 435/4; 435/7.1; 435/7.2; 435/283.1; 435/287.2; 530/300; 530/350

(58) Field of Classification Search
USPC ...... 530/300, 350; 204/194, 403; 435/283.1, 435/287.2, 4, 7.1, 7.2; 424/237.1
See application file for complete search history.

(56) References Cited

U.S. PATENT DOCUMENTS

| 4,956,296 | A | 9/1990 | Fahnestock |
| 4,977,247 | A * | 12/1990 | Fahnestock et al. ........... 530/350 |
| 6,133,431 | A | 10/2000 | Yasuda et al. |
| 6,365,418 | B1 | 4/2002 | Wagner et al. |
| 6,399,750 | B1 * | 6/2002 | Johansson ..................... 530/413 |
| 6,600,014 | B2 | 7/2003 | Ogino et al. |
| 2002/0182643 | A1 | 12/2002 | Marks et al. |
| 2005/0038228 | A1 | 2/2005 | Ogino et al. |
| 2005/0118646 | A1 | 6/2005 | Boniface et al. |

FOREIGN PATENT DOCUMENTS

| JP | 3-128400 A | 5/1991 |
| JP | 2006-504077 A | 2/2006 |
| KR | 2001-0005686 A | 1/2001 |
| WO | WO 97/26930 A1 | 7/1997 |
| WO | WO 98/42392 A1 | 10/1998 |
| WO | WO 00/53777 A1 | 9/2000 |
| WO | WO 02/36762 A1 | 6/2002 |
| WO | WO 03/025011 A1 | 3/2003 |
| WO | WO 2004/007669 A2 | 1/2004 |
| WO | WO 2005/078075 A2 | 8/2005 |
| WO | WO 2005/121178 A2 | 12/2005 |

OTHER PUBLICATIONS

Extended European Search Report, dated Sep. 24, 2010, for European Application No. 07747030.0.
Goward et al., "Expression and purification of a truncated recombinant streptococcal Protein G," Biochem. J., vol. 267, pp. 171-177, 1990.
Gülich et al., "Engineering streptococcal protein G for increased alkaline stability," Protein Engineering, vol. 15, No. 10, pp. 835-842, 2002.
Kobayashi et al., "Role of Side-chains in the Cooperative β-Hairpin Folding of the Short C-Terminal Fragment Derived from Streptococcal Protein G," Biochemistry, vol. 39, pp. 6564-6571, 2000 (Published on the Web May 5, 2000).
Linhult et al., "Evaluation of different linker regions for multimerization and coupling chemistry for immobilization of a proteinaceous affinity ligand," Protein Engineering, vol. 16, No. 12, pp. 1147-1152, 2003.
Boutillon et al., "Synthesis, three-dimensional structure, and specific 15N-labelling of the streptococcal protein G B1-domain", European Journal of Biochemistry, vol. 231, 1995, pp. 166-180.
Derrick et al., "The Third IgG-Binding Domain from Streptococcal Protein G", Journal of Molecular Biology, vol. 243, 1994, pp. 906-918.
European Office Action for Application No. 07747030.0 dated Sep. 15, 2011.
Guss et al., "Structure of the IgG-binding regions of streptococcal protein G", The EMBO Journal, vol. 5, No. 7, 1986, pp. 1567-1575.
International Search Report for Application No. PCT/KR2007/002996 dated Sep. 10, 2007.
Korean Notice of Allowance for Application No. 10-2007-0052560 dated Sep. 29, 2009.
Persson et al., "Purification and site-specific immobilization of genetically engineered glucose dehydrogenase on Thiopropyl-Sepharose", Federation of European Biochemical Societies 08835, vol. 270, No. 1, Sep. 2, 1990, pp. 41-44.
PNAS, Proceedings of the National Academy of Sciences of the United States of America, vol. 103, No. 32, Aug. 8, 2006, 11815-11816 (2 pages provided).
Office Action for Japanese Application No. 2009-517964, dated Sep. 25, 2012.
Japanese Office Action for Application No. 2009-517964 dated May 15, 2012 (with English translation).

* cited by examiner

*Primary Examiner* — Rodney P. Swartz
(74) *Attorney, Agent, or Firm* — Birch, Stewart, Kolasch & Birch, LLP (57) ABSTRACT

The present invention relates to an N-terminal cysteine-tagged Streptococcal protein G variant. Since the variant binds in a directional manner to a surface of a biochip or a biosensor, the variant provides a biochip and a biosensor having an improved antibody-immobilizing capability, compared with an untagged protein G variant.

15 Claims, 7 Drawing Sheets

40nm Gold particles

|  | Protein G immobilization(RU) | Antibody immobilization(RU) |
|---|---|---|
| N-terminal cystein-tagged protein G | 2168 RU | 396 RU |
| C-terminal cystein-tagged protein G | 2790 RU | 276 RU |

SEQUENCE LISTING

```
<160> NUMBER OF SEQ ID NOS: 9

<210> SEQ ID NO 1
<211> LENGTH: 55
<212> TYPE: PRT
<213> ORGANISM: Streptococcus sp.

<400> SEQUENCE: 1

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30
```

```
Ala Asn Asp Asn Gly Val Asp Gly Glu Trp Thr Tyr Asp Asp Ala Thr
        35                  40                  45

Lys Thr Phe Thr Val Thr Glu
    50                  55

<210> SEQ ID NO 2
<211> LENGTH: 55
<212> TYPE: PRT
<213> ORGANISM: Streptococcus sp.

<400> SEQUENCE: 2

Thr Tyr Lys Leu Val Ile Asn Gly Lys Thr Leu Lys Gly Glu Thr Thr
1               5                  10                  15

Thr Lys Ala Val Asp Ala Glu Thr Ala Glu Lys Ala Phe Lys Gln Tyr
            20                  25                  30

Ala Asn Asp Asn Gly Val Asp Gly Val Trp Thr Tyr Asp Asp Ala Thr
        35                  40                  45

Lys Thr Phe Thr Val Thr Glu
    50                  55

<210> SEQ ID NO 3
<211> LENGTH: 46
<212> TYPE: DNA
<213> ORGANISM: Artificial Sequence
<220> FEATURE:
<223> OTHER INFORMATION: Synthetic primer 1:sense

<400> SEQUENCE: 3
catatgtgcg acgacgacga caagaaaggc gaaacaacta ctgaag              46

<210> SEQ ID NO 4
<211> LENGTH: 49
<212> TYPE: DNA
<213> ORGANISM: Artificial Sequence
<220> FEATURE:
<223> OTHER INFORMATION: Synthetic primer 2: sense

<400> SEQUENCE: 4
catatgtgct gcgacgacga cgacaagaaa ggcgaaacaa ctactgaag           49

<210> SEQ ID NO 5
<211> LENGTH: 52
<212> TYPE: DNA
<213> ORGANISM: Artificial Sequence
<220> FEATURE:
<223> OTHER INFORMATION: Synthetic primer 3: sense

<400> SEQUENCE: 5
catatgtgct gctgcgacga cgacgacaag aaaggcgaaa caactactga ag       52

<210> SEQ ID NO 6
<211> LENGTH: 55
<212> TYPE: DNA
<213> ORGANISM: Artificial Sequence
<220> FEATURE:
<223> OTHER INFORMATION: Synthetic primer 6 :sense

<400> SEQUENCE: 6
catatgtgct gctgctgcga cgacgacgac aagaaaggcg aaacaactac tgaag    55

<210> SEQ ID NO 7
<211> LENGTH: 58
<212> TYPE: DNA
<213> ORGANISM: Artificial Sequence
```

-continued

```
<220> FEATURE:
<223> OTHER INFORMATION: Synthetic primer 7 :sense

<400> SEQUENCE: 7
catatgtgct gctgctgctg cgacgacgac gacaagaaag gcgaaacaac tactgaag        58

<210> SEQ ID NO 8
<211> LENGTH: 30
<212> TYPE: DNA
<213> ORGANISM: Artificial Sequence
<220> FEATURE:
<223> OTHER INFORMATION: Synthetic primer 8 :sense

<400> SEQUENCE: 8
ctcgagttca gttaccgtaa aggtcttagt                                       30

<210> SEQ ID NO 9
<211> LENGTH: 15
<212> TYPE: DNA
<213> ORGANISM: Artificial sequence
<220> FEATURE:
<223> OTHER INFORMATION: synthetic oligonucleotide fragment

<400> SEQUENCE: 9
gacgacgacg acaag                                                       15
```

CYSTEINE-TAGGED STREPTOCOCCAL PROTEIN G VARIANT

TECHNICAL FIELD

The present invention relates to an N-terminal cysteine-tagged Streptococcal protein G variant, a nucleic acid sequence, an expression vector, and a host cell encoding the same, a method for preparing the variant, and a biochip and a biosensor fabricated by using the variant or a polymer.

BACKGROUND ART

The antibody has been widely used in medical studies concerning diagnosis and treatment of diseases as well as in biological analyses, because of its property of specifically binding to an antigen (Fung et al., Curr. Opin. Biotechnol., 2001, 12, 65-69, and Heng Zhu et al., Curr. Opin. Chem. Biol., 2001, 5, 40-45). Recently, as an immunoassay, immunosensors have been developed, which require the immobilization of an antibody on a solid support and measure changes in current, resistance and mass, or optical properties or the like (Kim Rogers et al., Affinity Biosensors: Techniques and Protocols, 1998, Vol. 7). Among them, a surface plasmon resonance-based immunosensor making use of optical properties has been commercialized. The surface plasmon resonance-based biosensor provides qualitative information (whether two molecules specifically bind to each other) and quantitative information (reaction kinetics and equilibrium constants), and also performs sensing in real time without the use of labeling, thus being particularly useful for measuring antigen-antibody binding (Myszka, D. G., J. Mol. Recognit., 1999, Vol. 12, 390-408).

*In the immunosensor, it is very important that antibodies are selectively and stably immobilized on a solid support. The techniques for immobilizing antibodies are classified into two categories, physical immobilization and chemical immobilization. The physical immobilization techniques (Ferretti Paynter S S et al., Trends Anal. Chem., 2000, Vol. 19, 530-540) have been minimally used because they cause denaturation of the protein, and the results are less reproducible. In contrast, the chemical immobilization techniques (Nikin Patel et al., Langmuir, 1997, 13, 6485-6490) have been widely used because they show good reproducibility and a wide range of applications, due to their feature of allowing secure binding of proteins through covalent bonding. However, when immobilization of antibodies is performed using a chemical immobilization technique, the antibodies, being asymmetric macromolecules, often lose their orientation and activity to bind to antigens (Bin Lu et al., Analyst, 1996, 121, 29R-32R).

In an attempt to enhance the ability of antibodies to bind to antigens, a support may be used before the antibodies are linked to a solid substrate, and a technology of using protein G as the support is known. However, there is a problem that this protein G itself also loses orientation and its ability to bind to an antibody when bound to the support.

Accordingly, in order to solve such problem, a variety of methods have been suggested. For example, Streptococcal protein G is treated with 2-iminothiolane to perform phosphorylation of the amino acid group of a protein, and then the phosphorylated Streptococcal protein G is immobilized on an antibody. However, this method is directed to phosphorylating the amino groups of amino acids having an amino group (Arg, Asn, Gln, Lys), instead of phosphorylating any specific site, and thus the method results in low specificity and requires additional purification processes after chemical treatments (Y. M. Bae et al., Biosensors and Bioelectronics, 2005, 21, 103-110).

DISCLOSURE

Technical Problem

The present inventors have made extensive studies in order to solve the problem that antibodies lose their orientation upon binding to an immunosensor. As a result, they prepared an N-terminal cysteine-tagged protein G variant, and confirmed its usefulness through experiments.

Technical Solution

It is an object of the present invention to provide an N-terminal cysteine-tagged Streptococcal protein G variant, and a nucleic acid sequence encoding the same. The protein G is, for example, derived from *Streptocooccus*. The cysteine tag can be linked to the protein G through a linker.

It is another object of the present invention to provide an expression vector comprising the nucleic acid sequence encoding the cysteine-tagged protein G variant and a host cell transformed with the expression vector.

It is still another object of the present invention to provide a method for preparing a protein G variant, the method comprising a host cell containing the expression vector is cultured to express the protein G variant, and the protein G variant is isolated.

It is still another object of the present invention to provide a biosensor fabricated by linking the protein G variant to the surface of a solid support and a method for fabricating a biochip and a biosensor, in which the protein G variant is linked to the solid support with a thiol group.

DESCRIPTION OF DRAWINGS

In FIG. 3A,
Lane 1: protein size marker,
Lane 2: total protein of *E. coli* transformed with plasmid pET-cys1-L-proteinG,
Lane 3: soluble fraction protein of *E. coli* transformed with plasmid pET-cys1-L-proteinG,
Lane 4: non-soluble fraction protein of *E. coli* transformed with plasmid pET-cys1-L-proteinG,
Lane 5: total protein of *E. coli* transformed with plasmid pET-cys2-L-proteinG,
Lane 6: soluble fraction protein of *E. coli* transformed with plasmid pET-cys2-L-proteinG, Lane 7: non-soluble fraction protein of E. coli transformed with plasmid pET-cys2-L-proteinG, Lane 8: total protein of E. coli transformed with plasmid pET-cys3-L-proteinG, Lane 9: soluble fraction protein of E. coli transformed with plasmid pET-cys3-L-proteinG, Lane 10: non-soluble fraction protein of E. coli transformed with plasmid pET-cys3-L-proteinG, In FIG. 3B, Lane 1: protein size marker, Lane 2: total protein of E. coli transformed with plasmid pET-cys4-L-proteinG, Lane 3: soluble fraction protein of E. coli transformed with plasmid pET-cys4-L-proteinG, Lane 4: non-soluble fraction protein of E. coli transformed with plasmid pET-cys4-L-proteinG, Lane 5: total protein of E. coli transformed with plasmid pET-cys5-L-proteinG, Lane 6: soluble fraction protein of E. coli transformed with plasmid pET-cys5-L-proteinG, Lane 7: non-soluble fraction protein of E. coli transformed with plasmid pET-cys5-L-proteinG.

Lane 1: protein size marker,

Lane 2: Antibodies directly bound to gold nano-particle,

Lane 3: Protein G not tagged with cysteine were immobilized on gold nano-particles and then antibodies were bound thereto, Lane 4: Immobilizing protein G variants tagged with one cysteine residue onto gold nano-particles, Lane 5: Immobilizing protein G variants tagged with two cysteine residues onto gold nano-particles, Lane 6: Immobilizing protein G variants tagged with three cysteine residues onto gold nano-particles.

BEST MODE

According to an embodiment to achieve the above objects of the present invention, the present invention relates to a cysteine-tagged Streptococcal protein G variant, having the following structure:

$Met_x$-$(Cys)n$-$L_y$-protein G-$Q_z$ wherein Met represents methionine; L represents a linker; protein G comprises two antibody-binding domains (B1,B2); Q represents a tag for protein purification; x, y, and z are each 0 or 1; and n is a number from 1 to 10.

Protein G is a bacterial cell wall protein isolated from group G streptococci, and has been known to bind to Fc and Fab regions of a mammalian antibody (Hoffman W L et al., J. Immuunol. Methods, 1988 Aug. 9, 112, 113-120). However, the protein G has been known to bind to the Fc region with an affinity about 10 times than the Fab region. A DNA sequence of native protein G was analyzed and has been disclosed. A Streptococcal protein G variant and Streptococcal protein A are one of various proteins related to cell surface, which are found in Gram-positive bacteria, and have the property of binding to an immunoglobulin antibody. The Streptococcal protein G variant, inter alia, is more useful than the Streptococcal protein A, since the Streptococcal protein G variant can bind to a wider range of mammalian antibodies, so as to be used as a suitable receptor for the antibodies.

In the present invention, the origin of the protein G is not particularly limited, and the native protein G, of which amino acid sequence is modified by deletion, addition, substitution or the like, may be suitably used for the purpose of the present invention, as long as it holds the ability to bind to an antibody. In Examples of the present invention, only the antibody-binding domains (B1, B2) of the Streptococcal protein G were used.

Figure 1:
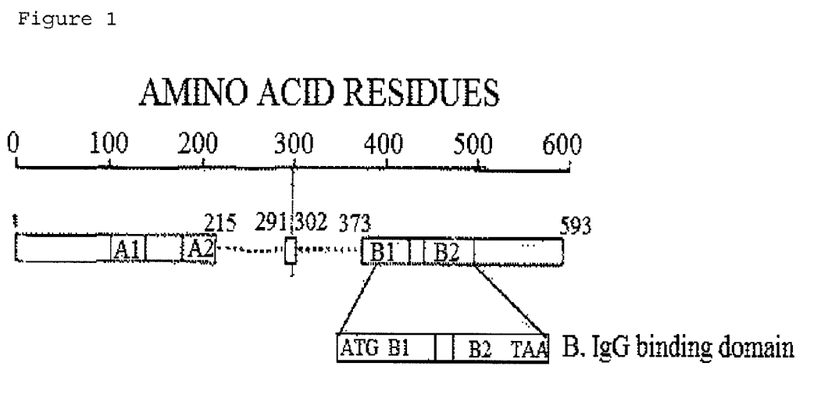
FIG. 1 shows binding domains (B1, B2) of Streptococcal protein G that binds with antibodies.

The protein G-B1 domain consists of three β-sheets and one α-helix, and the third β-sheet and α-helix in its C-terminal part are involved in binding to the immunoglobulin G. The B1 domain is represented by SEQ ID NO:1, and the B2 domain is represented by SEQ ID NO:2. As the amino acid sequences of B1 and B2 domains are compared to each other, there are differences in four sequences, but little difference between their structures. In the Example of the invention, a B1 domain, in which ten amino acids were deleted at its N-terminal, was used (FIG. 1). It was reported that even though a form of the B1 domain having ten amino acid residues deleted from the N-terminal side was used, there was no impact on the function of binding with an antibody (Christopher R. GOWARD et al., Biochem. J., 1990, 267, 171-177, Jeremy P. Derrick et al., J. Mol. Biol., 1994, 243, 906-918, and Kobayashi N et al., Biochemistry, 2000 May 30, 39, 6564-6571).

As used herein, the term "cysteine tag ((Cys)n)" refers to a peptide consisting of one or more cysteine residues, which is fused at the N-terminal of protein G. Examples of the cysteine tag include a tag consisting of 1 to 10 cysteine residues, preferably a tag consisting of 1 to 5 cysteine residues, and more preferably a tag consisting of 1 to 3 cysteine residues.

In the protein G variant of the present invention, the cysteine tag may be directly linked to the protein G by a covalent bond, or may be linked through a linker. The linker is a peptide having any sequence, which is inserted between the protein G and cysteine. The linker may be a peptide consisting of 2 to 10 amino acid residues. In the Examples of the invention, the linker having 5 amino acid residues was used. The cysteine tag of the invention was not inserted inside of the protein G, and provides the protein G with orientation on attaching to a solid support. If the linker is attached, a thiol group is readily exposed to the outside. Thus, the protein G can be more efficiently bound to a biosensor with directionality.

In order to easily isolate the protein G variant of the present invention, a tag (Q) for protein purification may be further included at its C-terminal. In the Examples of the present invention, a hexahistidine was tagged at its C-terminal, but as the tag for protein purification, any known tag can be used for the purpose of the invention without being limited thereto. The variant of the invention may contain methionine, which serves as an initiation codon in prokaryotes, or not. In the Examples of the present invention, each of the variants was prepared to be linked with one to five cysteines.

The present invention relates to nucleic acid sequence encoding the protein G variant, an expression vector comprising the same, and a host cell transformed with the expression vector. The vector is any vehicle that allows DNA insertion into a host cell to express the protein G variant, and includes vectors such as plasmid vector, cosmid vector, and bacteriophage vector, preferably plasmid vector. For the purpose of the invention, the expression vector may include expression regulatory elements such as a promoter, an initiation codon, a termination codon, a polyadenylation signal, and an enhancer.

Figure 2:
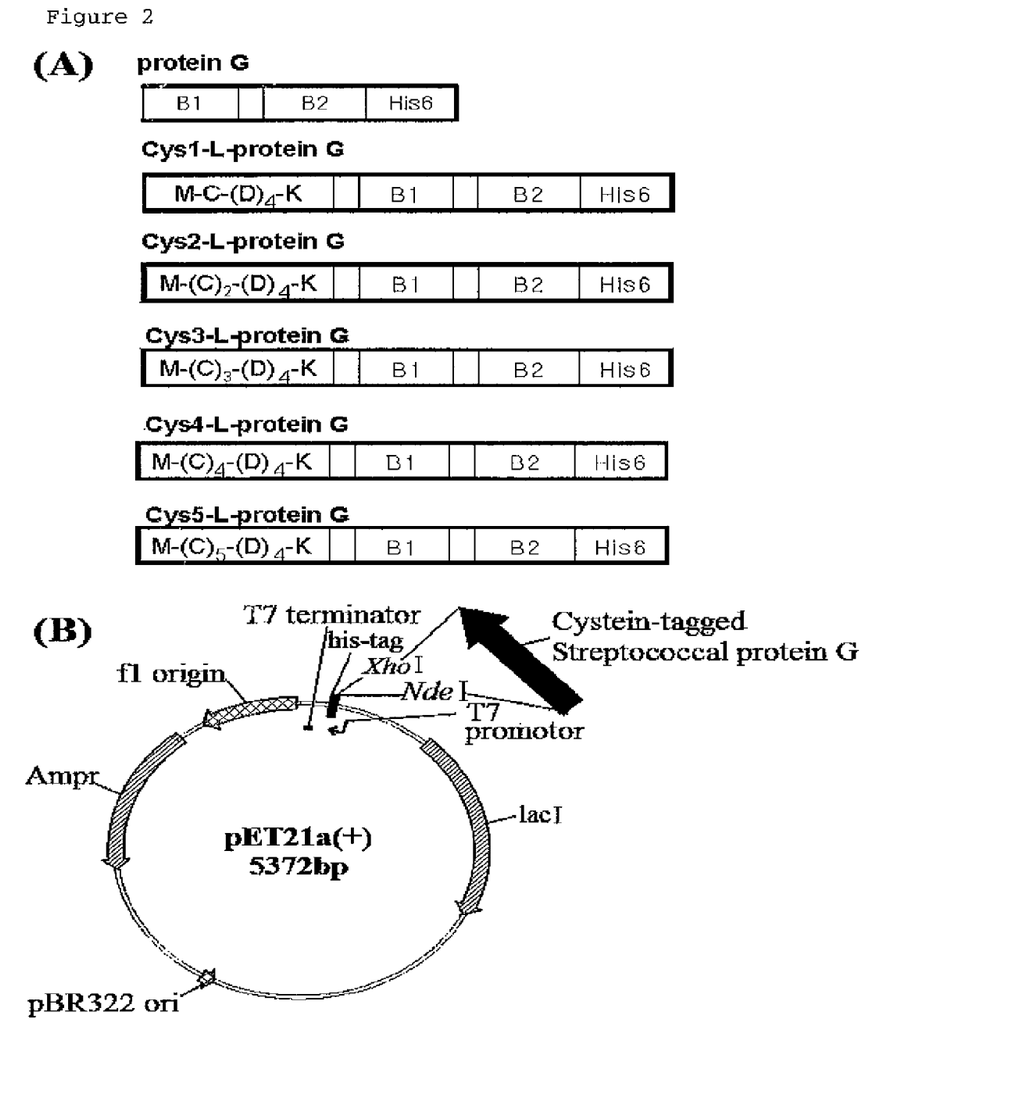
FIG. 2A shows a fragment for protein G preparation and five fragments for protein G variant preparation.
FIG. 2B shows a method for preparing an expression vector for the preparation of protein G variants, in which Streptococcal protein G is tagged with 1 to 5 cysteine residues, by inserting the fragments into the vector (pET-cys1-L-proteinG, pET-cys2-L-proteinG, pET-cys3-L-proteinG, pET-cys4-L-proteinG, pET-cys5-L-proteinG, cys: cysteine, L: linker, four asparagine residues and one lysine residue, protein G: structure of Streptococcal protein G).
Figure 3:
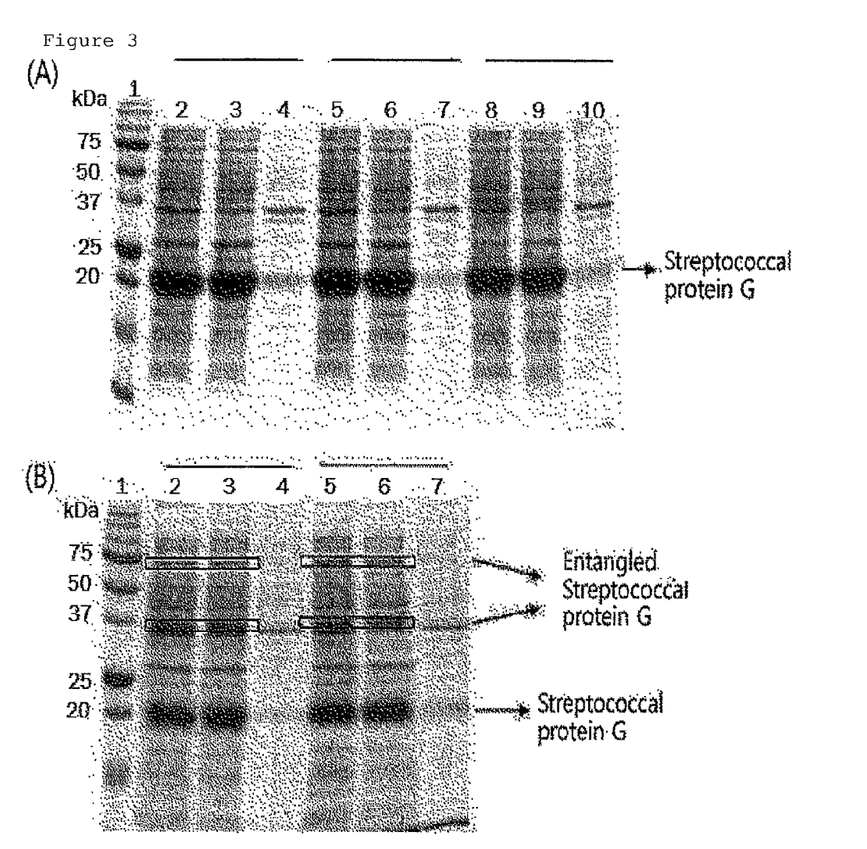
FIG. 3A and FIG. 3B are photographs of protein electrophoresis (SDS-PAGE) showing the expression patterns of the cysteine-tagged Streptococcal protein G variants in *E. coli*. The descriptions of lanes in FIG. 3A and FIG. 3B are as follows.

In the embodiments, expression vectors comprising the nucleic acid sequences that encode the Streptococcal protein G variants tagged with 1 to 5 cysteine residues at their N-terminal (pET-cys1-L-proteinG, pET-cys2-L-proteinG, pET-cys3-L-proteinG, pET-cys4-L-proteinG, pET-cys5-L-proteinG), were prepared as shown in FIG. 2. FIG. 3 is a photograph of protein electrophoresis (SDS-PAGE) showing the expression patterns of the cysteine-tagged proteins, which are expressed in *E. coli* transformed with the expression vectors.

Any host cell capable of expressing the protein G variant of the present invention can be used. Examples of the host cell include *E. coli* and *Bacillus subtilis*.

The protein G variants of the present invention can be prepared by a peptide synthesis method, in particular, efficiently prepared by a genetic engineering method. The genetic engineering method is a method for expressing large amounts of the desired protein in a host cell such as *E. coli* by gene manipulation, and the related techniques are described in detail in disclosed documents (Bernard. R Glick et al., Molecular Biotechnology: Principle and Application of Recombinant DNA; ASM Press: 1994, Vol $2^{nd}$ edition, and Wiseman. A, J. Chem. Technol. Biotechnol., 1993, 56, 3-13).

Cysteine is an amino acid having a thiol group, and has been known to specifically immobilize a protein by its insertion into the protein (Persson M et al., FEBS Lett., 1990 Sep. 17, 270, 41-44, and Kallwass H. K. W et al., Biotechnol. Lett., 1993, 15, 29-34). Disclosed is a method for binding cysteine at the C-terminal of Streptococcal protein G. However, in the present invention, cysteine having a thiol group was used to tag the N-terminal, which is remote from the active domain of the Streptococcal protein G variant. The active domain of the Streptococcal protein G that binds with an antibody is located in its C-terminal (the third β-sheet and α-helix). Accordingly, cysteine was not used to tag the inside of the protein G variant but at the N-terminal thereof, thereby minimizing the loss of antibody-binding ability, in which the loss can occur by tagging the C-terminal with cysteine residues.

Figure 9:
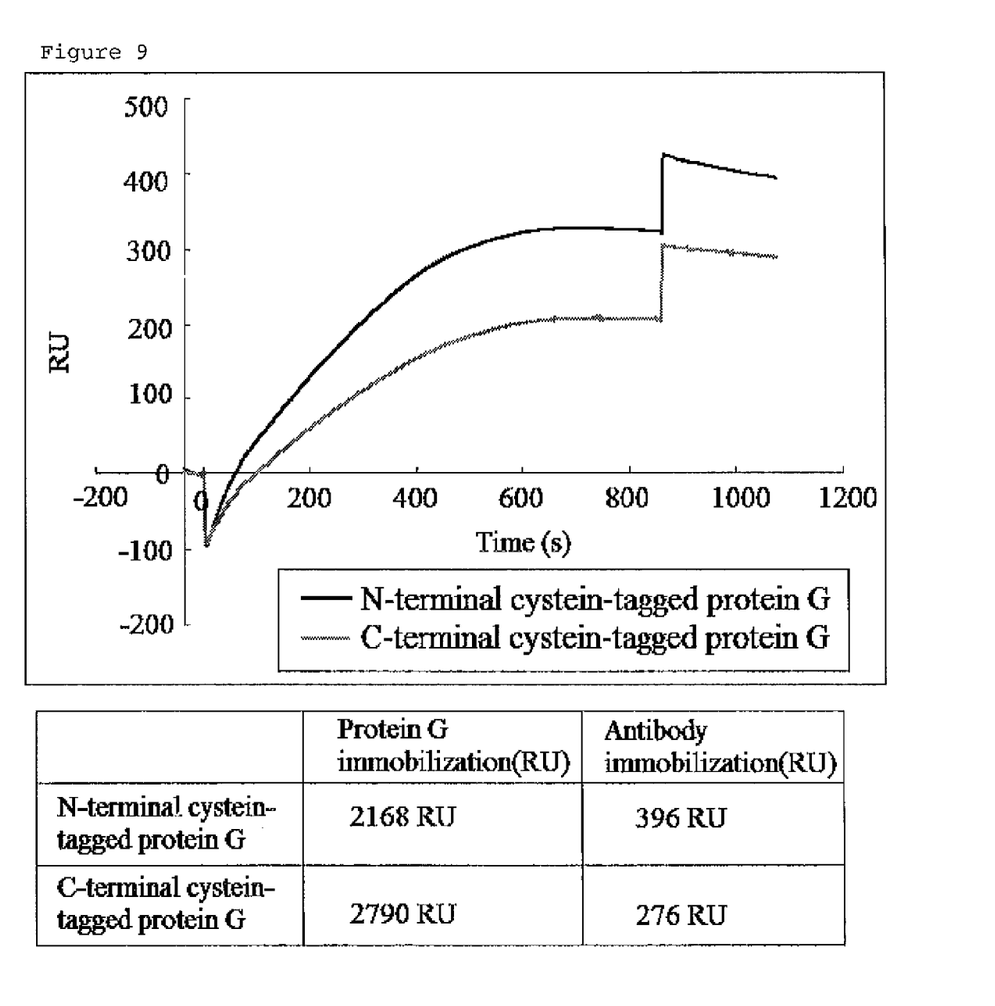
FIG. 9 shows the results of measurement of the binding capability of an antibody, expressed by changes in the surface plasmon resonance signal, using a surface plasmon resonance (SPR)-based biosensor in which an N-terminal cysteine-tagged protein G variant and a C-terminal cysteine-tagged protein G variant are bound to a gold thin film surface.

In a specific embodiment to confirm this, the present inventors measured the antibody-binding ability, after binding each of N-terminal cysteine-tagged protein G variant and C-terminal cysteine-tagged protein G variant to the surface of a gold thin film, by detecting the changes in surface plasmon resonance signal using a surface plasmon resonance-based biosensor (SPR). It was confirmed that when the same concentrations of an N-terminal cysteine-tagged protein G variant and a C-terminal cysteine-tagged protein G variant were bound to the surface of the gold thin film, the similar amounts of proteins were bound thereto. Then, the antibody-binding abilities of an N-terminal cysteine-tagged protein G variant and a C-terminal cysteine-tagged protein G variant were confirmed by reacting with a low concentration of antibody (0.5 μg/ml). As a result, when they were reacted with 0.5 μg/ml of antibody, the antibody-binding abilities of N-terminal cysteine-tagged protein G variant immobilized on the support was about 30% higher than that of C-terminal cysteine-tagged protein G variant immobilized on the support (N-terminal: 396RU, C-terminal: 276RU). Based on the above result, the antibody-binding ratio of N-terminal cysteine-tagged protein G variant immobilized on the support was found to be higher than that of C-terminal cysteine-tagged protein G variant immobilized on the support in a low concentration. Therefore, it was confirmed that the N-terminal cysteine tag was distant from the C-terminal of the cysteine-tagged protein G variant, which is an active domain to domain with the antibody, and thus the loss of antibody-binding ability of the protein G was minimized (FIG. 9).

In embodiments of the present invention, Streptococcal protein G variants, to which each of one, two, three, four, and five cysteines was bound, were prepared (Example 2). Transformed *E. coli* capable of expressing each protein G variants were prepared and deposited at the Korean Collection for Type Cultures (KCTC), which is located at #52, Oun-dong, Yusong-ku, Taejon 306-333, Republic of Korea, on May 22, 2006 under the Budapest Treaty and obtained the accession numbers: KCTC 10948BP, KCTC 10949BP, KCTC 10950BP, KCTC 10951BP and KCTC 10952BP, respectively. KCTC 10948BP strain was transformed with the vector pET-M-cys1-L-protein G and expresses a protein G variant with one cysteine; KCTC 10949BP strain was transformed with the vector pET-M-cys2-L-protein G and expresses a protein G variant with two cysteines; KCTC 10950BP strain was transformed with the vector pET-M-cys3-L-protein G and expresses a protein G variant with three cysteines; KCTC 10951BP strain was transformed with the vector pET-M-cys-4-L-protein G and expresses a protein G variant with four cysteines; KCTC 10952BP strain was transformed with the vector pET-M-cys5-L-protein G and expresses a protein G variant with five cysteines. Gene manipulation was performed according to the above invention, and then each of the manipulated genes was inserted into the protein expression vector. Each of the proteins was expressed, and separated by protein electrophoresis. At this time, in the case of tagging 1 to 3 cysteine residues, the active form of recombinant Streptococcal protein G variant was produced even more.

In another embodiment, the present invention relates to a method for fabricating a biochip and a biosensor by binding the protein G variant to the surface of a solid support. Examples of the solid support include metal or membrane, ceramic, glass, polymer surface or silicone, as described in the following Table 1.

TABLE 1

Substrate for self-assembled monolayer formation of protein having cysteine group

| Presence or absence of surface chemical pretreatment | Type of Substrate | Thin film. surface | Nano-particle ornano-structure |
|---|---|---|---|
| Absence | Ag | o | |
| | Ags | | o |
| | Au | o | o |
| | CdSe | | o |
| | CdS | | o |
| | AuAg | | o |
| | AuCu | | o |
| | Cu | o | o |
| | FePt | | o |
| | GaAs | o | |
| | Ge | o | |
| | Hg | o | |
| | Pd | o | o |
| | Pt | o | o |
| | Stainless Steel 316L | o | |
| | Zn | o | |
| | ZnSe | o | |
| | PdAg | | o |
| | Ru, Ir | | o |
| Presence (maleimide group, epoxygroup, nitrophenol proline group, and methyl iodide group) | Membrane | o | |
| | Ceramics | o | |
| | Glass | o | |
| | Polymer surface | o | |
| | Silicone | o | | o: applicable substrate

Figure 4:
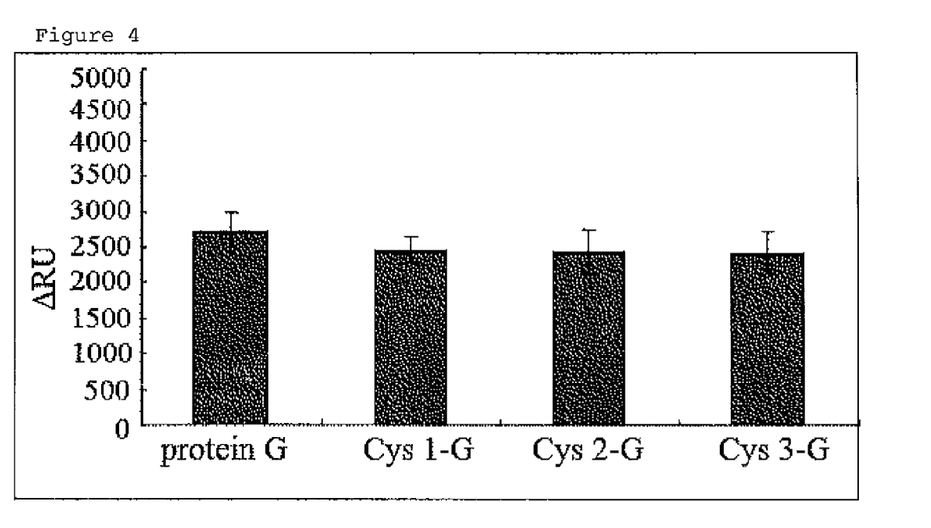
FIG. 4 is a graph showing changes in the surface plasmon resonance signal measured after binding four different types of Streptococcal protein G variants to the surface of gold thin film (four different types of Streptococcal protein G; protein G: as a control, Streptococcal protein G having no thiol group, cys1-G: Streptococcal protein G with one cysteine residue, cys2-G: Streptococcal protein G with two cysteine residues, cys3-G: Streptococcal protein G with three cysteine residues).
Figure 5:
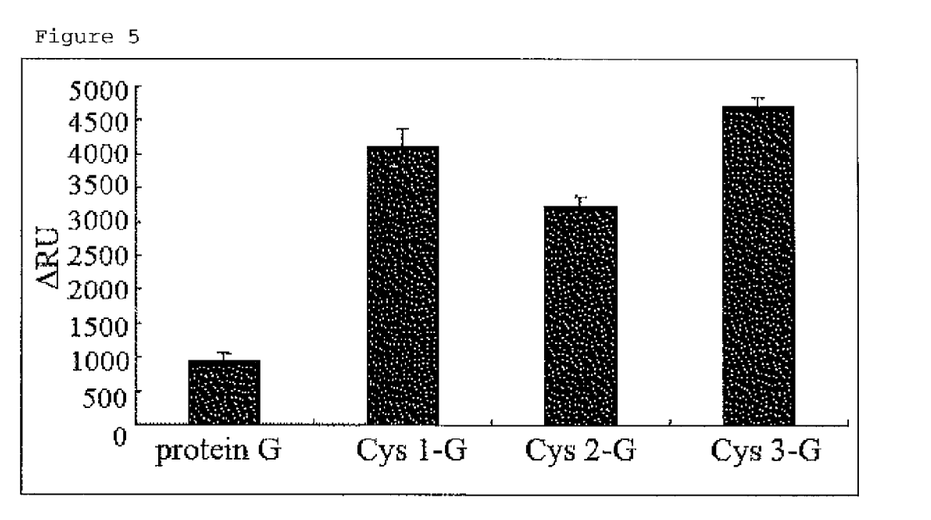
FIG. 5 is a graph showing changes in the surface plasmon resonance signal obtained by reacting a human antibody on a layer formed by four different types of Streptococcal protein G variants (identical to those illustrated in FIG. 4) bound to a gold thin film surface.

In a preferred specific embodiment of the present invention, a biochip and biosensor, in which the prepared protein G variant is directly bound to a metal surface (gold, silver, copper, iron, platinum, zinc, etc.) and a semiconductor and then immobilized, are provided. In the present invention, the changes in surface plasmon resonance signal were measured using the surface plasmon resonance-based biosensor (SPR) to detect in real time the reaction of adsorbing the cysteine-tagged protein G variants to the surface of the gold thin film. As a result, there is little difference in the surface plasmon resonance signals of the recombinant protein tagged with one to three cysteine residues (average about 2400 RU) and an untagged recombinant protein (average about 2700 RU) (FIG. 4). However, when the recombinant protein tagged with one to three cysteine residues and the untagged recombinant protein were bound to the surface of the gold thin film, and then bound to antibodies, the change in the surface plasmon resonance signals of the recombinant protein tagged with one cysteine residue increased by about 4 times (4000 RU), the same change of the recombinant protein tagged with two cysteine residues increased by about 3.2 times (3200 RU), and the same change of the recombinant protein tagged with three cysteine residues increased by about 4.8 times (4800 RU), as compared to the change of the untagged recombinant protein (1000 RU) (FIG. 5). Therefore, it was confirmed that the protein G variants of the present invention are very useful for immobilizing antibodies on the surface of the gold thin film.

Figure 6:
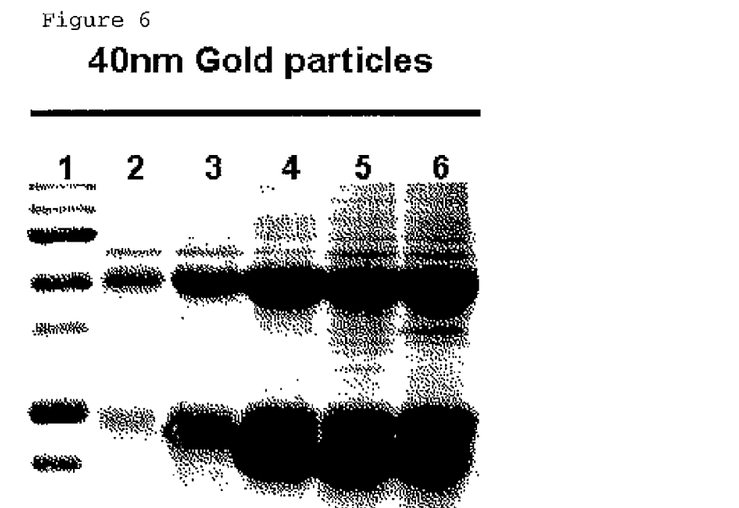
FIG. 6 is a photograph of protein electrophoresis showing the condition of antibody immobilization obtained by immobilizing four different types of Streptococcal protein G variants (identical to those illustrated in FIG. 4) onto gold nanoparticles and then binding an antibody. The descriptions of lanes in FIG. 6 are as follows.

According to still another specific embodiment of the present invention, gold nano-particles, which bind to antibodies through the cysteine-tagged Streptococcal protein G variant, are provided. After binding the untagged recombinant protein and the recombinant Streptococcal protein G variants tagged with one, two, and three cysteine residues onto the gold nano-particles, the patterns of binding with antibodies were confirmed by protein electrophoresis. As a result, when the antibodies were reacted after binding the Streptococcal protein G variants on the gold nano-particles, much more antigens were bound thereto than when the antibodies were reacted only with the gold nano-particles. Further, the recombinant Streptococcal protein G variants tagged with one, two, and three cysteine residues bound with a larger number of antigens than the untagged recombinant protein. From the results, it was confirmed that the cysteine-tagged recombinant Streptococcal protein G variants are very useful for immobilizing antigens on the gold nano-particles (FIG. 6).

According to still another specific Example, the present invention relates to a biosensor, in which the thiol group of the cysteine tag of the invention covalently bonded to a maleimide group, an epoxy group, a nitrophenol proline group, and a methyl iodide group that are bound to ceramics, glass, polymers, silicones, membranes, or the like, so as to immobilize the protein G variant on the solid support, and then the antibodies are bound thereto.

Figure 7:
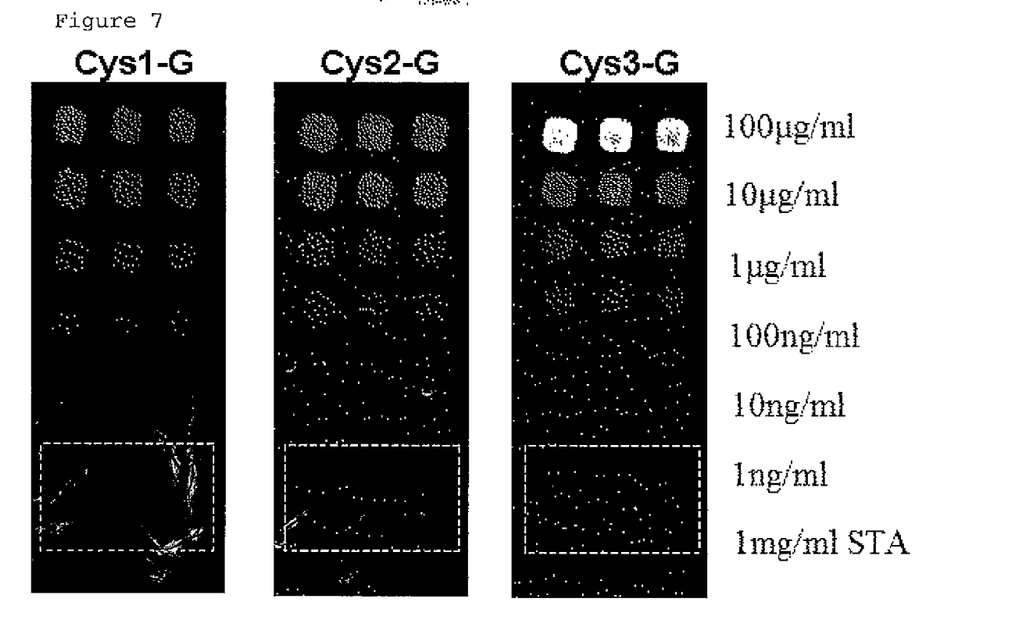
FIG. 7 is a photographic image obtained using a fluorescence scanner, by immobilizing cysteine-tagged Streptococcal protein G variants onto a glass surface to which maleimide group is bound, and then forming, on the glass surface, an array of a Monoclonal anti-biotin Cy3 antibody labeled with a fluorescent marker, and Streptavidin-Cy3 as a control using a microarrayer.

In the embodiments of the present invention, after specifically binding the Streptococcal protein G variants to the maleimide groups on the glass surface through the thiol groups of cysteine tags having one, two, and three cysteine residues, an array was fabricated with antibodies labeled with a fluorescent marker and streptavidin-Cy3 as a control using a microarrayer. Then, the degree of specific binding of protein and the effect of non-specific binding were measured using a fluorescent scanner. As a result, the fluorescent signal of Streptavidin-Cy3 (1 mg/ml) was not observed. The fluorescent signals increased as the concentration of monoclonal anti-biotin-Cy3 antibody increased, which indicates that the Streptococcal protein G variants tagged with one, two, and three cysteine residues specifically bound to antibodies. Further, when each of the Streptococcal protein G variants with the same concentrations was reacted with the antibodies, they showed high binding abilities even with a low concentration of the antibodies. Consequently, it was confirmed that the recombinant Streptococcal protein G tagged with one, two, and three cysteine residues is useful for immobilizing antibodies on the glass surface having a maleimide group (FIG. 7).

In still another specific embodiment of the present invention, the present invention relates to a method for detecting an antigen using a biosensor, the method comprising fabricating the biosensor by immobilizing a protein G variant on the solid support, and then binding an antibody thereto.

Figure 8:
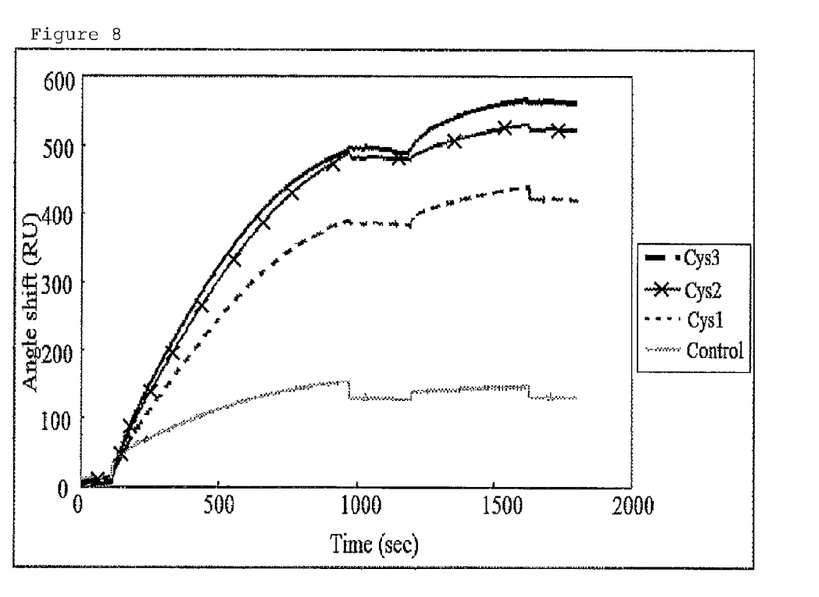
FIG. 8 is a graph showing changes in the surface plasmon resonance signal obtained by allowing an antibody against PSA (0.5 µg/ml) to react on a layer formed by four different types of Streptococcal protein G variants (identical to those illustrated in FIG. 4) bound to a gold thin film surface, and then allowing the antigen PSA (0.5 µg/ml) to react therewith.

After binding the recombinant protein without being tagged with cysteine and the recombinant Streptococcal protein G variants tagged with one, two, and three cysteine residues on the surface of the gold thin film and then immobilizing the antibodies, the changes in surface plasmon resonance signal were measured using the surface plasmon resonance-based biosensor (SPR) in order to detect antigen binding. When an antigen-antibody binding event occurs, a high concentration of antibodies has been known to inhibit the recognition of the antigen (Y. M. Bae et al., Biosensors and Bioelectronics, 2005, 21, 103-110). Therefore, a low concentration of antibodies (0.5 µg/ml) was immobilized, and then reacted with the antigens. As a result, when antibodies were bound (anti-human Kallikrein 3/PSA antibody, R&D systems), the change in the surface plasmon resonance signals of the untagged recombinant protein increased by 114 RU, that of the recombinant protein tagged with one cysteine residue increased by 472 RU, that of the recombinant protein tagged with two cysteine residues increased by 376 RU, and that of the recombinant protein tagged with three cysteine residues increased by 491 RU. Then, antigens (Recombinant Human kallikrein 3/PSA, 0.5 μg/ml) were reacted with the antibodies. As a result, the change in the surface plasmon resonance signals of the untagged recombinant protein increased by 7 RU, the same change of the recombinant protein tagged with one cysteine residue increased by 49 RU, the same change of the recombinant protein tagged with two cysteine residues increased by 41 RU, and the same change of the recombinant protein tagged with three cysteine residues increased by 74 RU. From the results, it was found that the recombinant protein tagged with three cysteine residues effectively facilitates binding with the antigen (FIG. 8).

Hereinafter, the present invention will be described in detail with reference to Examples. However, these Examples are for illustrative purposes only, and the invention is not intended to be limited thereto.

MODE FOR INVENTION

Example 1

Protein Expression Analysis of Cysteine-tagged Streptococcal Protein G Variant

<1-1> Gene Preparation of Streptococcal Protein G Variants Tagged with One, Two, Three, Four, and Five Cysteine Residues Six primers were prepared in order to tag with one, two, three, four, and five cysteine residues at the N-terminal. In the base sequence of five sense primers of the six primers, an initiation codon (ATG) was followed by 1 to 5 cysteine codons (TGC), and in order to provide a link to protein G, GAC GAC GAC GAC AAG (SEQ ID NO: 9) (four Asp codons and one Lys codon) were included. Furthermore, in order to insert the gene into an expression vector pET21a (Novagen), the NdeI restriction enzyme cleavage site was introduced into the N-terminal primer and the XhoI restriction enzyme cleavage site was introduced into the C-terminal primer. To obtain the genomic gene of Streptococcus, a polymerase chain reaction (PCR) was performed with the primers (base pairs of SEQ ID NO:3 and SEQ ID NO:8, base pairs of SEQ ID NO:4 and SEQ ID NO:8, base pairs of SEQ ID NO:5 and SEQ ID NO:8, base pairs of SEQ ID NO:6 and SEQ ID NO:8, base pairs of SEQ ID NO:7 and SEQ ID NO:8). Thus, only the amino acid regions (B1 [a form having 10 initial amino acid residues cleaved], B2), which are known as domains to which an antibody binds, were obtained. The obtained fragments were cleaved with the restriction enzymes, which were the same enzymes as introduced into each primer. Then, the cleaved fragment were inserted into the pET21a vector cleaved with NdeI and XhoI restriction enzymes to prepare pET-cys1-L-proteinG, pET-cys2-L-proteinG, pET-cys3-L-proteinG, pET-cys-4-L-proteinG, and pET-cys5-L-proteinG vectors (FIG. 2). The expression vectors express Met at the N-terminal.

```
Primer 1: sense
                                                        (SEQ ID NO: 3)
5'-CATATGTGCGACGACGACGACAAGAAAGGCGAAACAACTACTGAAG-3'

Primer 2: sense
                                                        (SEQ ID NO: 4)
5'-CATATGTGCTGCGACGACGACGACAAGAAAGGCGAAACAACTACTGAAG-3'

Primer 3: sense
                                                        (SEQ ID NO: 5)
5'-CATATGTGCTGCTGCGACGACGACGACAAGAAAGGCGAAACAACTACTGAAG-3'

Primer 4: sense
                                                        (SEQ ID NO: 6)
5'-CATATGTGCTGCTGCTGCGACGACGACGACAAGAAAGGCGAAACAACTACTGAAG-3'

Primer 5: sense
                                                        (SEQ ID NO: 7)
5'-CATATGTGCTGCTGCTGCTGCGACGACGACGACAAGAAAGGCGAAACAACTACTGAAG-3'

Primer 6: antisense
                                                        (SEQ ID NO: 8)
5'-CTCGAGTTCAGTTACCGTAAAGGTCTTAGT-3'
```

<1-2> Photograph of Protein Electrophoresis Showing Expression of Streptococcal Protein G Variants Tagged with One, Two, Three, Four, and Five Cysteines E. coli BL21 cells were transformed with the prepared pET-cys1-L-proteinG, pET-cys2-L-proteinG, pET-cys3-L-proteinG, pET-cys4-L-proteinG, and pET-cys5-L-proteinG, and shaking-cultured at 37° C. until an O.D. (optical density, A600 nm) became 0.6. Then, IPTG (isopropyl β-D-thiogalactopyranoside, total concentration of 1 mM) was added thereto, so as to induce protein expression at 25° C. After 14 hours, the E. coli cells were centrifuged, and the obtained cell pellets were disrupted by sonication (Branson, Sonifier450, 3 KHz, 3 W, 5 min) to give a total protein solution. The total protein solution was separated by centrifugation into a solution of soluble fraction proteins and a solution of non-soluble proteins. The protein solutions obtained in the above were mixed with a buffer solution (12 mM Tris-Cl, pH 6.8, 5% glycerol, 2.88 mM mercaptoethanol, 0.4% SDS, 0.02% Bromophenol Blue) and heated at 100° C. for 5 minutes, and then the resultant was loaded on a polyacrylamide gel, which consisted of a 1 mm-thick 15% separating gel (pH 8.8, width 20 cm, length 10 cm) covered by a 5% stacking gel (pH 6.8, width 10 cm, length 12.0 cm). Subsequently, electrophoresis was performed at 200 to 100V and 25 mA for 1 hour, and the gel was stained with a Coomassie staining solution to confirm the recombinant protein.

The descriptions of lanes in FIGS. 3A and 3B are as follows.

In FIG. 3(A),

Lane 1: protein size marker,

Lane 2: total protein of E. coli transformed with plasmid pET-cys1-L-proteinG,

Lane 3: soluble fraction protein of *E. coli* transformed with plasmid pET-cys1-L-proteinG,
Lane 4: non-soluble fraction protein of *E. coli* transformed with plasmid pET-cys1-L-proteinG,
Lane 5: total protein of *E. coli* transformed with plasmid pET-cys2-L-proteinG,
Lane 6: soluble fraction protein of *E. coli* transformed with plasmid pET-cys2-L-proteinG,
Lane 7: non-soluble fraction protein of *E. coli* transformed with plasmid pET-cys2-L-proteinG,
Lane 8: total protein of *E. coli* transformed with plasmid pET-cys3-L-proteinG,
Lane 9: soluble fraction protein of *E. coli* transformed with plasmid pET-cys3-L-proteinG,
Lane 10: non-soluble fraction protein of *E. coli* transformed with plasmid pET-cys3-L-proteinG,
In FIG. 3(B),
Lane 1: protein size marker,
Lane 2: total protein of *E. coli* transformed with plasmid pET-cys4-L-proteinG,
Lane 3: soluble fraction protein of *E. coli* transformed with plasmid pET-cys4-L-proteinG,
Lane 4: non-soluble fraction protein of *E. coli* transformed with plasmid pET-cys4-L-proteinG,
Lane 5: total protein of *E. coli* transformed with plasmid pET-cys5-L-proteinG,
Lane 6: soluble fraction protein of *E. coli* transformed with plasmid pET-cys5-L-proteinG,
Lane 7: non-soluble fraction protein of *E. coli* transformed with plasmid pET-cys5-L-proteinG.
Protein produced from plasmid pET-cys1-L-proteinG: cys1-G
Protein produced from plasmid pET-cys2-L-proteinG: cys2-G
Protein produced from plasmid pET-cys3-L-proteinG: cys3-G
Protein produced from plasmid pET-cys4-L-proteinG: cys4-G
Protein produced from plasmid pET-cys5-L-proteinG: cys5-G <1-3> Streptococcal Proteins Tagged with One, Two or Three Cysteine Residues Expression and Purification of G Variant and Control (Streptococcal Protein G Variant not Tagged with Cysteine)

To purify a soluble protein solution obtained after the expression as described in <1-2>, a solution of disrupted cells in which the six recombinant genes conjugated with hexahistidine were expressed, was loaded on a column packed with IDA excellulose. The six recombinant proteins conjugated with histidine were eluted with an eluent (50 mM Tris-Cl, 0.5 M imidazole, 0.5 M NaCl, pH 8.0). The eluted protein solution was dialyzed in PBS (phosphate buffer saline, pH 7.4) buffer solution.

Example 2

Binding Streptococcal Protein G Variants Tagged with One, Two or Three Cysteine Residues and an Untagged Streptococcal Protein G Variant Recombinant Protein to the Surface of a Gold Thin Film to Immobilize the Antibody: Detecting the Reaction of Binding the Variant Recombinant Protein on the Surface to the Surface of a Gold Thin Film and Immobilizing the Antibody, Through a Surface Plasmon Resonance Sensor by Means of Changes in the Surface Plasmon Resonance Signal A gold thin film chip was treated with a mixed solution (65° C.) of 95% sulfuric acid and 30% aqueous hydrogen peroxide (volume ratio 3:1) for 30 minutes, and then the chip was washed sequentially with double distilled water, ethanol and double distilled water. Subsequently, the chip was dried with nitrogen gas and mounted on a BIA-core surface plasmon resonance sensor. 150 µl each of 200 µg/ml solutions of recombinant proteins tagged with one, two and three cysteine residues, respectively, and of an untagged recombinant protein were introduced to the gold thin film surface of the mounted chip at a flow rate of 5 µl/min, so as to immobilize the proteins. After reacting the gold thin film surface and the aforementioned proteins, 100 µl of BSA (3 mg/ml) was introduced at a flow rate of 5 µl/min to prevent non-specific reactions. Subsequently, 100 µl of an antibody (100 µg/ml, human IgG, Sigma) was introduced at a flow rate of 5 µl/min to produce a biosensor in which protein G variant and the antibody were immobilized on a gold thin film, and the changes in the plasmon resonance signals were measured (FIG. 5).

Example 3

Binding Streptococcal Protein G Variants Tagged with One, Two or Three Cysteine Residues and an Untagged Streptococcal Protein G Variant to Gold Nano-particles and Immobilizing an Antibody: Binding Streptococcal Protein G Variants Tagged with One, Two or Three Cysteine Residues and an Untagged Streptococcal Protein G Variant to Gold Nano-particles, Immobilizing an Antibody, and Confirming the Antibody with Protein Electrophoresis Gold nano-particles with 2.5 O.D./ml were washed with PBS buffer solution, and then were reacted with 100 µl each of a series of Streptococcal protein G variants (200 µg/ml) at 4° C. for 16 hours. The reaction product was reacted with 10 µl of an antibody (3.5 g/ml, anti-rabbit IgG (Whole Molecule)-TRITC conjugate, Sigma) at ambient temperature for 2 hours. Furthermore, as a control, gold nano-particles with 2.5 O.D./ml were reacted with 10 µl of the antibody (3.5 g/ml) at ambient temperature for 2 hours. After completion of the reactions, the reaction products were centrifuged to remove any unreacted antibody molecules, and the resultant was washed with PBS buffer solution.

Thereafter, the proteins bound to gold nano-particles were confirmed by protein electrophoresis. Captions for the lanes shown in FIG. 6 are as follows.

Lane 1: protein size marker.
Lane 2: Antibodies directly bound to gold nano-particle.
Lane 3: Protein G not tagged with cysteine were immobilized on gold nano-particles and then antibodies were bound thereto.
Lane 4: Immobilizing protein G variants tagged with one cysteine residue onto gold nano-particles.
Lane 5: Immobilizing protein G variants tagged with two cysteine residues onto gold nano-particles.
Lane 6: Immobilizing protein G variants tagged with three cysteine residues onto gold nano-particles.

As a result, a larger number of antigen molecules were bound to the gold nano-particles which were conjugated with Streptococcal protein G variants and reacted with antibodies, compared with the gold nano-particles which were reacted with antibodies only. Also, a larger number of antigen molecules were bound to the recombinant Streptococcal protein G variants tagged with one, two or three cysteine residues, compared with the untagged recombinant protein. From the above results, it was confirmed that cysteine-tagged recombinant Streptococcal protein G variants were useful in immobilizing antibodies onto gold-nanoparticles (FIG. 6).

Example 4

Reacting Streptococcal Protein G Variants Tagged with One, Two or Three Cysteine Residues with Maleimide Groups Formed on Glass Surface to Immobilize Antibodies: Conjugating the Above-modified Recombinant Proteins with Maleimide Groups, which Covalently Bind to Thiol Groups, on the Glass Surface, and Measuring the Specific Antibody-binding Reaction Using a Fluorescence Scanner A glass surface was immersed in a piranha solution (sulfuric acid:hydrogen peroxide, 3:1 v/v) and allowed to react in an oven at 90° C. for 20 minutes. After the reaction, the glass surface was washed with water and ethanol, and then was immersed in ethanol containing 1% APTS ((3-Aminopropyl) trimethoxysilane, 09326, SIGMA-ALDRICH) for 15 to 20 minutes to react, so as to provide an aminated surface. After completion of the reaction, the glass surface was washed with ethanol, and subsequently heated in an oven at 100° C. until the time of use. The prepared aminated surface was immersed in a 10 mM solution of BMPS(N-[b-Maleimidopropyloxy] succinimide ester, 22298, PIERCE, USA) dissolved in DMSO (dimethyl sulfoxide, D2650, SIGMA-ALDRICH) to react for about 30 minutes. The maleimide groups provided on the final glass surface, which groups would be covalently bonded to SH groups, were reacted with Streptococcal protein G variants tagged with one, two or three cysteine residues on the glass surface to immobilize the protein. On the surface where a series of Streptococcal protein G variants were immobilized, an antibody labeled with a fluorescent labeling substance, monoclonal anti-biotin Cy3 (C5585, SIGMA-ALDRICH), and a control, streptavidin-Cy3 (streptavidin-Cy3 from *Streptomyces avidinii*, S6420 SIGMA-ALDRICH) were arranged into an array using a microarrayer, and then the degree of specific protein binding and the effect of non-specific binding were measured using a fluorescence scanner. As a result, no fluorescent signal of Streptavidin-Cy3 (1 mg/ml) was detected, and since the fluorescent signal increased with an increase in the concentration of the antibody, Monoclonal anti-biotin Cy3, it was confirmed that the antibody reactions with Streptococcal protein G variants tagged with one, two and three cysteine residues were specifically achieved. Also, when the antibody was reacted after allowing the Streptococcal protein G variants to react at the same concentration, the reaction occurred at a low concentration of the antibody with a high binding power. From this, it was confirmed that the recombinant Streptococcal protein G variants tagged with one, two and three cysteine residues are useful for immobilizing antibodies on a glass surface where maleimide group is attached (FIG. 7).

Example 5

Binding Streptococcal Protein G Variants Tagged with One, Two or Three Cysteine Residues an Untagged Streptococcal Protein G Variant Recombinant Protein to the Surface of a Gold Thin Film, and then Allowing an Antigen-antibody Reaction to Occur: Binding the Modified Recombinant Proteins on the Surface to the Surface of a Gold Thin Film to Immobilize the Antibody, and then Measuring the Antigen-sensing Reaction by Means of Changes in the Surface Plasmon Resonance Signal Using a Surface Plasmon Resonance Sensor A gold thin film chip was treated with a mixed solution (65° C.) of 95% sulfuric acid and 30% aqueous hydrogen peroxide (volume ratio 3:1) for 30 minutes, and then the chip was washed sequentially with double distilled water, ethanol and double distilled water. Subsequently, the chip was dried with nitrogen gas and mounted on a BIA-core surface plasmon resonance sensor. 150 µl each of 200 µg/ml solutions of recombinant proteins tagged with one, two and three cysteine residues, respectively, and of an untagged recombinant protein (control) were introduced to the gold thin film surface of the mounted chip at a flow rate of 5 µl/min, so as to immobilize the proteins. After reacting the gold thin film surface and the aforementioned proteins, 100 µl of BSA (3 mg/ml) was introduced at a flow rate of 5 µl/min to prevent non-specific reactions. Subsequently, 100 µl of an antibody (0.5 µg/ml, anti-human Kallikrein 3/PSA antibody, R&D systems) was introduced at a flow rate of 5 µl/min, and the biosensor with immobilized antibody and 50 µl of an antigen (0.5 µg/ml, Recombinant Human Kallikrein 3/PSA) were allowed to react. Then, changes in the plasmon resonance signal were detected (FIG. 8).

INDUSTRIAL APPLICABILITY

The cysteine-tagged protein G variant according to the present invention binds in a directional manner to the solid support of a biosensor by its thiol group, thus to efficiently bind to antibodies. Thus, the cysteine-tagged protein G variant can be satisfactorily used in biochips and biosensors which utilize antigen-antibody reactions.

The invention claimed is:

1. An N-terminal cysteine-tagged Streptococcal protein G variant, represented by the following formula:

Met$_x$-(Cys)n-L$_y$-protein G-Q$_z$ wherein Met is methionine; L is a linker; protein G comprises two antibody-binding domains B1 and B2 of protein G obtained from *Streptococcus*; Q is a tag for protein purification; x, y and z are each 0 or 1; and n is a number from 1 to 10, wherein the antibody-binding domain B1 is represented by SEQ ID NO: 1, and the antibody-binding domain B2 is represented by SEQ ID NO: 2, and wherein the antibody-binding domain B1 has a deletion of 10 amino acid residues at its N-terminus.

2. The N-terminal cysteine-tagged Streptococcal protein G variant according to claim 1, wherein the cysteine tag consists of 1 to 5 cysteine residues.

3. The N-terminal cysteine-tagged Streptococcal protein G variant according to claim 1, wherein the cysteine tag consists of three cysteine residues.

4. The N-terminal cysteine-tagged Streptococcal protein G variant according to claim 1, wherein the linker consists of four asparagine residues and one lysine residue.

5. A nucleic acid sequence encoding the N-terminal cysteine-tagged Streptococcal protein G variant according to claim 1.

6. An expression vector comprising the nucleic acid sequence according to claim 5.

7. A host cell selected from the group consisting of KCTC 10948BP, KCTC 10949BP, KCTC 10950BP, KCTC 10951BP and KCTC 10952BP, wherein the host cell comprises the expression vector according to claim 6.

8. A method for producing a protein G variant, the method comprising culturing the host cell according to claim 7, and separating the protein G variant therefrom.

9. A biochip or biosensor comprising the N-terminal cysteine-tagged Streptococcal protein G variant according to claim 1, wherein the protein G variant is immobilized on a surface of a solid support.

10. The biochip or biosensor according to claim 9, wherein the solid support is selected from ceramics, glass, polymer, silicone and metal.

11. The biochip or biosensor according to claim 10, wherein the metal is gold.

12. The biochip or biosensor according to claim 9, further comprising an antibody which binds to the cysteine-tagged Streptococcal protein G variant immobilized on the surface of a solid support.

13. The biochip or biosensor according to claim 9, wherein the surface of the solid support is modified with any one group selected from a maleimide group, an epoxy group, a nitrophenol proline group and a methyl iodide group.

14. The biochip or biosensor according to claim 13, wherein the cysteine-tagged Streptococcal protein G variant is covalently bonded through a thiol group to any one of a maleimide group, an epoxy group, a nitrophenol proline group and a methyl iodide group on the surface of the solid support.

15. A method of analyzing an antigen using the biochip or biosensor according to claim 12.

* * * * *